(12) United States Patent
Tsubouchi et al.

(10) Patent No.: US 11,266,809 B2
(45) Date of Patent: Mar. 8, 2022

(54) FLUSHABLE CATHETER DEVICE

(71) Applicant: TERUMO KABUSHIKI KAISHA, Tokyo (JP)

(72) Inventors: Takeshi Tsubouchi, Ann Arbor, MI (US); Yusuke Sekine, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 588 days.

(21) Appl. No.: 16/166,552

(22) Filed: Oct. 22, 2018

(65) Prior Publication Data

US 2019/0054271 A1 Feb. 21, 2019

Related U.S. Application Data

(63) Continuation of application No. PCT/JP2017/015799, filed on Apr. 19, 2017.

(30) Foreign Application Priority Data

May 18, 2016 (JP) .............................. JP2016-099758

(51) Int. Cl.
*A61M 25/00* (2006.01)
*A61B 5/157* (2006.01)
(Continued)

(52) U.S. Cl.
CPC ..... *A61M 25/0068* (2013.01); *A61B 5/15003* (2013.01); *A61B 5/155* (2013.01);
(Continued)

(58) Field of Classification Search
CPC .............. A61M 1/3643; A61M 1/0084; A61M 1/0209; A61M 1/0058; A61M 2025/0019;
(Continued)

(56) References Cited

U.S. PATENT DOCUMENTS

| 6,749,617 | B1 * | 6/2004 | Palasis | ............... | A61B 17/3468 |
| | | | | | 606/167 |
| 8,416,536 | B2 | 4/2013 | Fuchino et al. | | |

(Continued)

FOREIGN PATENT DOCUMENTS

JP 2013165891 A 8/2013

OTHER PUBLICATIONS

International Search and Opinion Report for PCT/JP2017/015799, dated Jun. 20, 2017.

*Primary Examiner* — Nathan R Price
*Assistant Examiner* — Courtney B Fredrickson
(74) *Attorney, Agent, or Firm* — MacMillan, Sobanski & Todd, LLC (57) ABSTRACT

A flushable catheter device has an outer tube with a first distal end opening to be introduced into a blood vessel and defining a first lumen. An inner tube is disposed in the first lumen with a second distal end opening proximally spaced from the first distal end opening and defining a second lumen. A space axially disposed between the end openings defines an outflow/inflow inhibiting portion which inhibits a flow of fluid out from the first lumen into the into the vessel as a result of a perfusion of a flushing fluid being supplied through the first lumen and into the second lumen.

7 Claims, 9 Drawing Sheets

(51) Int. Cl.
  *A61B 5/155*    (2006.01)
  *A61B 5/15*    (2006.01)
  *A61M 1/00*    (2006.01)
  *A61M 1/02*    (2006.01)
  *A61M 1/36*    (2006.01)

(52) U.S. Cl.
  CPC ........ *A61B 5/157* (2013.01); *A61B 5/150992* (2013.01); *A61M 1/0209* (2013.01); *A61M 1/85* (2021.05); *A61M 25/003* (2013.01); *A61B 5/150389* (2013.01); *A61B 5/150503* (2013.01); *A61M 1/3643* (2013.01); *A61M 25/0021* (2013.01); *A61M 2025/0019* (2013.01); *A61M 2025/0039* (2013.01)

(58) Field of Classification Search
  CPC .............. A61B 5/155; A61B 5/150992; A61B 5/15003; A61B 5/150366
  See application file for complete search history.

(56) References Cited

U.S. PATENT DOCUMENTS

| | | | | |
|---|---|---|---|---|
| 2003/0216685 | A1* | 11/2003 | Porter | A61B 17/12136 604/82 |
| 2007/0078444 | A1* | 4/2007 | Larsson | A61M 1/0031 604/540 |
| 2013/0023770 | A1* | 1/2013 | Courtney | A61B 8/12 600/467 |
| 2014/0163530 | A1 | 6/2014 | Frenkel | |
| 2015/0224284 | A1* | 8/2015 | Panotopoulos | A61M 25/09 604/43 |

* cited by examiner

FLUSHABLE CATHETER DEVICE

CROSS REFERENCE TO RELATED APPLICATIONS

This application is a continuation of PCT Application No. PCT/JP2017/015799, filed Apr. 19, 2017, based on and claiming priority to Japanese Application No. 2016-099758, filed May 18, 2016, both of which are incorporated herein by reference in their entirety.

BACKGROUND OF THE INVENTION

The present invention relates to a catheter and a catheter device.

In the related art, a catheter device, which collects blood by inserting a distal end of a catheter into a blood vessel, is known. There are cases where air or a residue of blood or the like is present inside a catheter, and if blood is collected by using such a catheter, air or a residue inside the catheter flows into a blood vessel sometimes. Therefore, it is desirable that air and a residue are removed by performing flushing in which a catheter is cleaned with a flushing liquid such as a physiological salt solution, before blood is collected.

For example, U.S. Pat. No. 5,335,658 discloses a catheter device in which blood is collected via a catheter and air or a residue of blood or the like inside the catheter can be removed by flushing the catheter.

When a catheter is flushed, a flushing liquid is supplied in a direction toward a distal end of the catheter inserted into a blood vessel. On the other hand, when blood is collected, aspiration is performed from the distal end toward a proximal end, which is the opposite direction. Therefore, a fluid passing through the catheter flows in directions opposite to each other between a case of flushing and a case of collecting blood. In this manner, due to a fluid moving back and forth inside the catheter, there are cases where a residue such as air inside a catheter could flow out into a blood vessel.

In addition, when a catheter is flushed, for example, there are cases where a large amount of a flushing liquid is supplied to the inside of the catheter in order to remove a residue of blood or the like which is less likely to be removed and has adhered to an inner wall of the catheter. Accordingly, there is a possibility that a large amount of a flushing liquid will flow out into a blood vessel and an undesirable load injected to a patient will increase.

SUMMARY OF THE INVENTION

An object of the present invention is to provide a catheter and a catheter device, in which a flushing liquid, air, or a residue of blood or the like is inhibited from flowing out into a blood vessel, and blood collecting and flushing can be performed in a noninvasive manner.

In order to achieve the object described above, there is provided a catheter including an outer tube which includes a first distal end opening portion to be introduced into a living body and in which a first lumen capable of circulating a fluid is formed. An inner tube is disposed in the first lumen, which includes a second distal end opening portion which is spaced proximally from the first distal end opening portion, and in which a second lumen capable of circulating a fluid is formed. An outflow/inflow inhibiting portion is partitioned in the first lumen between the first distal end opening portion and the second distal end opening portion and inhibits a fluid from flowing out from the first lumen or a fluid from flowing into the first lumen via the first distal end opening portion, due to a perfusion of a fluid which is supplied to the first lumen and flows to the second lumen.

According to an embodiment, the catheter device includes a supply section which supplies a flushing liquid to the first lumen, an aspiration unit which aspirates a fluid via the second lumen, and a control unit which controls operations of the supply section and the aspiration unit. The control unit controls operations of the supply section and the aspiration unit to form a perfusion of the flushing liquid, which is supplied to the first lumen and is aspirated into the second lumen, in the outflow/inflow inhibiting portion and inhibits a fluid from flowing out from the first lumen or a fluid from flowing into the first lumen via the first distal end opening portion, due to the perfusion.

According to the catheter and the catheter device having the configurations as described above, blood can be collected from a living body via the first distal end opening portion of the outer tube. In addition, when a catheter is flushed, the outflow/inflow inhibiting portion inhibits a flushing liquid, air, or a residue of blood or the like from flowing out into a blood vessel via the first distal end opening portion, and blood can be inhibited from flowing into the first lumen via the first distal end opening portion. Accordingly, blood collecting and flushing can be performed in a noninvasive manner.

DETAILED DESCRIPTION OF PREFERRED EMBODIMENTS

Hereinafter, with reference to the drawings, embodiments of the present invention will be described. The following description does not limit the technical scope or meaning of the terms disclosed in Patent. In addition, for the convenience of description, there are cases where the dimensional ratios of the drawings are exaggerated and are different from the actual ratios.

First Embodiment

Figure 1:
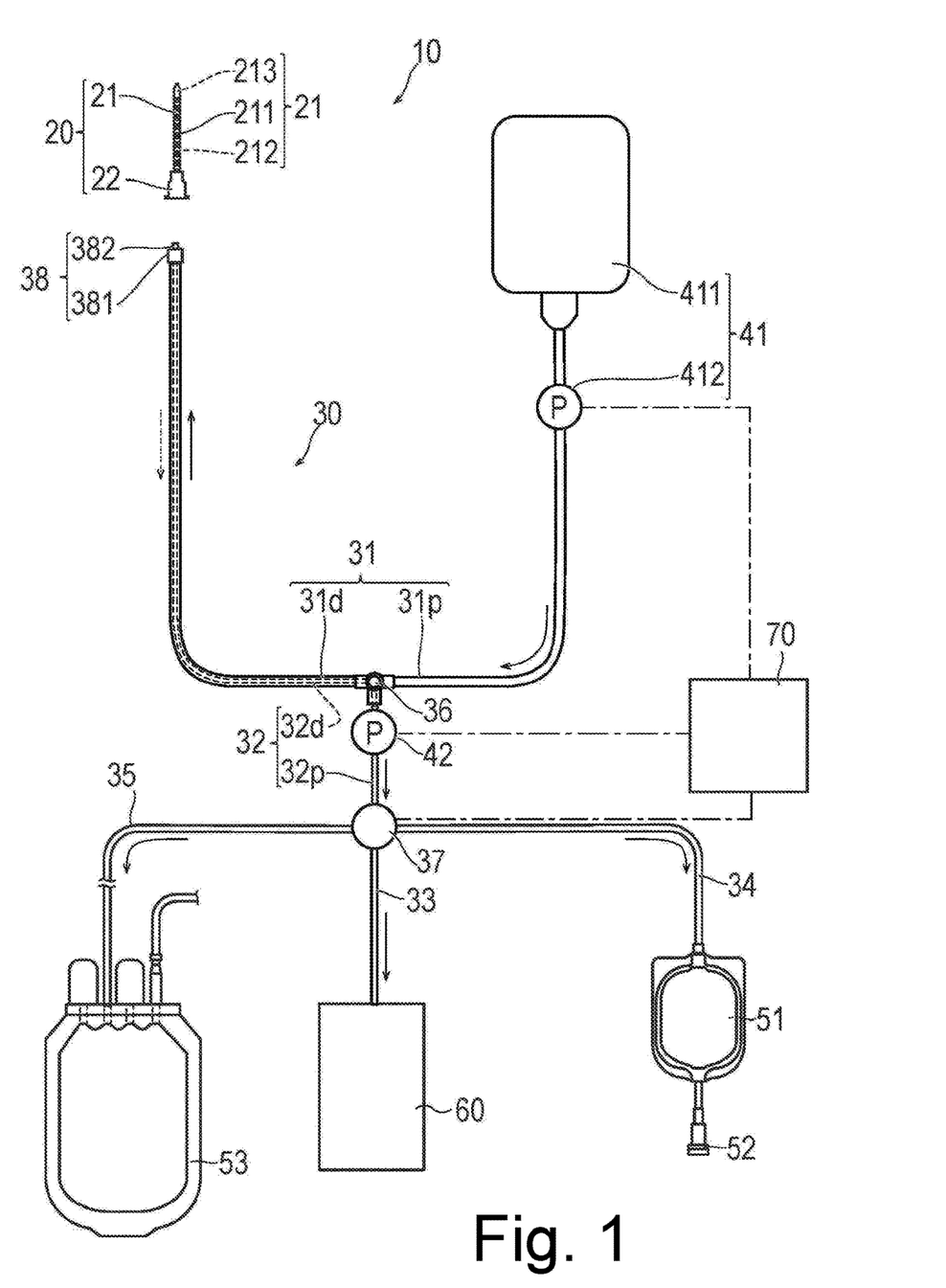
FIG. 1 is a view schematically illustrating the entirety of a catheter device and system according to a first embodiment.
Figure 2:
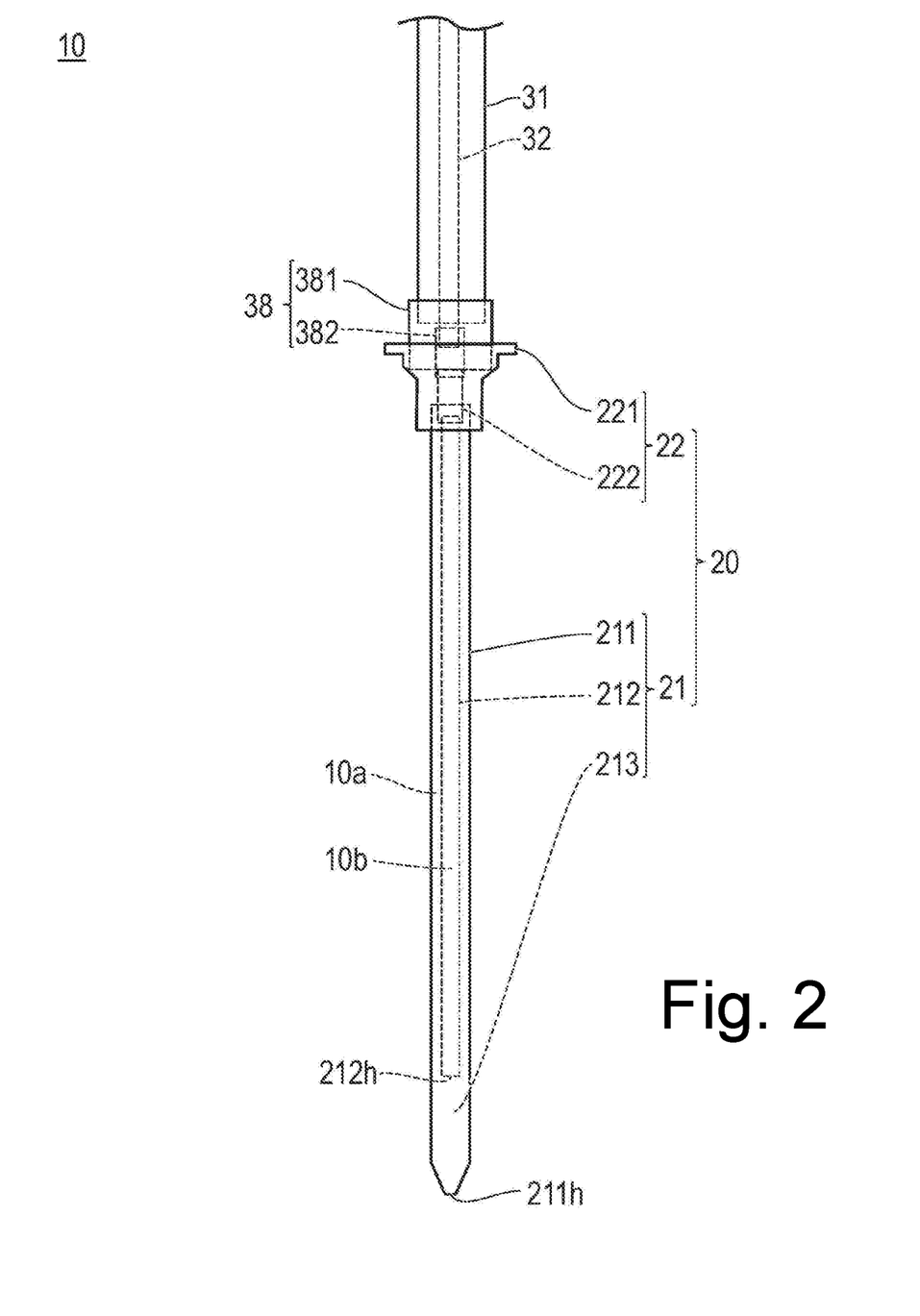
FIG. 2 is a side view illustrating a distal portion of a catheter according to the first embodiment.
Figure 3:
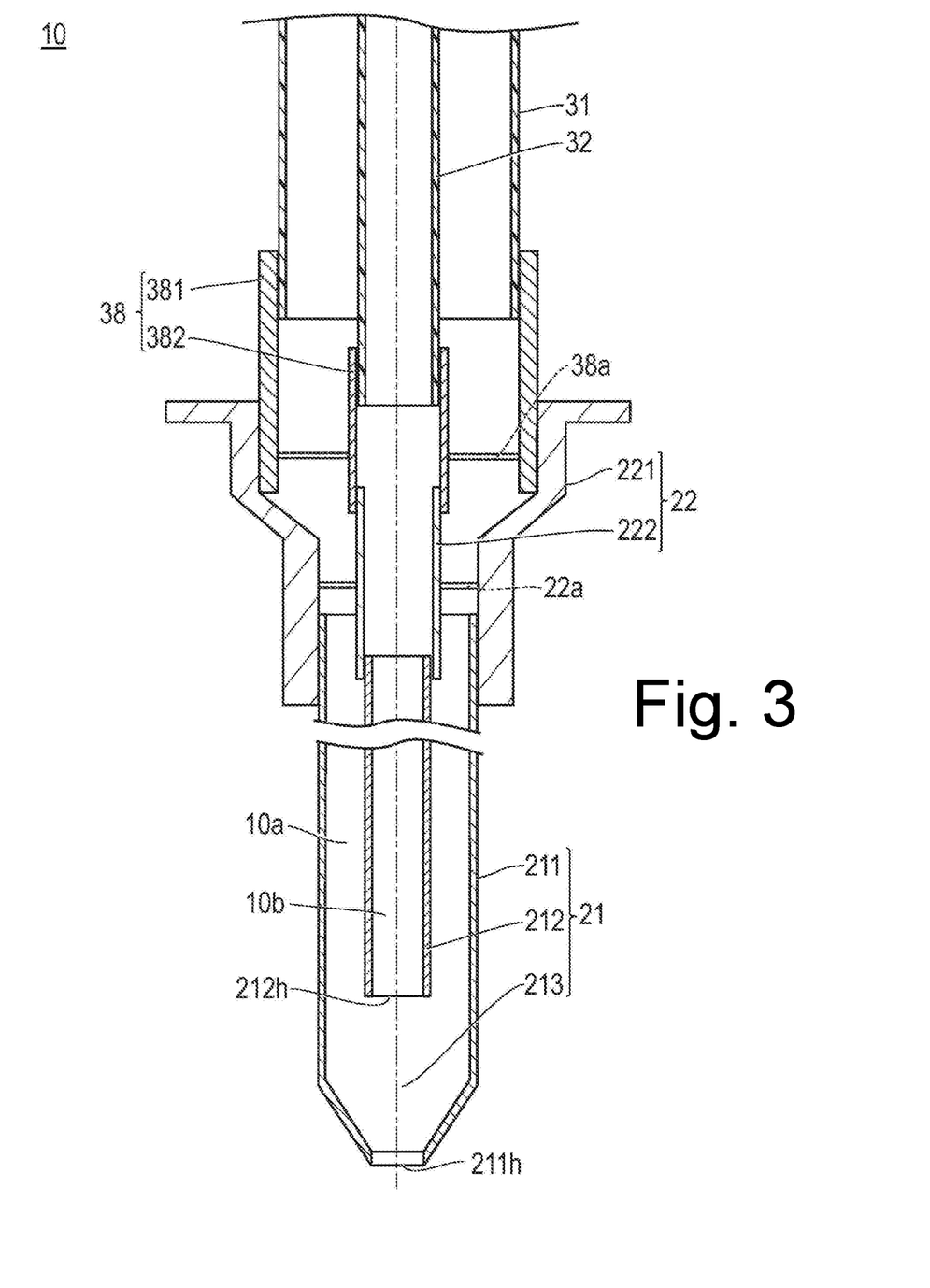
FIG. 3 is a sectional view illustrating the distal portion of the catheter according to the first embodiment.

With reference to FIGS. 1 to 3, a catheter device 1 according to a first embodiment of the present invention will be described.

The catheter device 1 according to the first embodiment is a device which can separately store initial inflowing blood that is firstly collected and blood that is later collected through a main blood collection process, wherein the catheter device can be flushed. Generally, when a living body is punctured with a blood collecting needle, bacteria present on skin or under the skin are likely to be incorporated into the collected blood. Therefore, it has been known that there is a high possibility of bacteria incorporated into initially flowing blood. According to the catheter device 1, it is possible to collect blood having less impurities such as bacteria by performing flushing of the device after initial flowing blood is collected and then performing the main blood collection. In addition, initially flowing blood can be utilized for the purpose of a blood analysis process which may be tolerant of the presence of impurities.

As illustrated in FIG. 1, the catheter device 1 includes a catheter 10 which selectably circulates a fluid such as blood or a flushing liquid, a supply section 41 which supplies a flushing liquid to the catheter 10, an aspiration pump (corresponding to an aspiration unit) 42 which aspirates a fluid from the catheter 10, an initial flowing blood bag 51 which stores firstly collected inflowing blood, a sampling port 52 which is connected to a proximal side of the initial flowing blood bag 51, a main blood collecting bag 53 which stores collected blood other than the initially collected blood, a waste liquid tank 60 which stores a fluid to be discarded, and a control unit 70 which controls an operation of each part of the catheter device 1. Hereinafter, the configuration of each part will be described.

The catheter 10 has a blood collecting needle 20 which punctures a living body and of which a distal portion is inserted into a blood vessel, and a catheter main body 30 which is connected to the proximal side of the blood collecting needle 20.

In this specification, a side on which the blood collecting needle 20 to be inserted into a living body is disposed will be referred to as a "distal end" or a "distal side", and a side on which the supply section 41, the initial flowing blood bag 51, the main blood collecting bag 53, and the waste liquid tank 60 are disposed will be referred to as a "proximal end" or a "proximal side". Consistent with usage in the art, the distal portion denotes a certain range including the distal end (outermost distal end) and the periphery thereof, and a proximal portion denotes a certain range including the proximal end (innermost proximal end) and the periphery thereof.

As illustrated in FIG. 2, the blood collecting needle 20 includes a needle body 21 which has a double tube structure and punctures a blood vessel, and a hub 22 which is disposed on the proximal side of the needle body 21.

The needle body 21 has an outer tube 211 in which a first lumen 10a capable of circulating a fluid is formed, an inner tube 212 which is disposed in the first lumen 10a and in which a second lumen 10b capable of circulating a fluid is formed, and an outflow/inflow inhibiting portion (i.e., space) 213.

The outer tube 211 has a substantially elongated cylindrical shape. The outer tube 211 has a first distal end opening portion 211h, which penetrates tissue of a living body to be introduced into a blood vessel, at the distal end thereof. It is preferable that the distal end of the outer tube 211 has a sharp needle tip such that the living body is easily punctured.

The inner tube 212 has a substantially elongated cylindrical shape. The inner tube 212 has a second distal end opening portion 212h at the distal end thereof. The second distal end opening portion 212h is disposed to be spaced by a short distance from first distal end opening portion 211h (i.e., positioned slightly closer to the proximal side than the first distal end opening portion 211h).

As indicated with a dashed line in FIG. 3, a central axis of the outer tube 211 is configured to coincide with a central axis of the inner tube 212. Accordingly, the first lumen 10a formed in a gap between the outer tube 211 and the inner tube 212 has a uniform size in a circumferential direction. Therefore, a uniform flow having no turbulence can be formed in the first lumen 10a.

For example, the outer tube 211 and the inner tube 212 can be formed of a metal or a resin material.

The outflow/inflow inhibiting portion 213 is an extension of the first lumen 10a between the first distal end opening portion 211h and the second distal end opening portion 212h. The outflow/inflow inhibiting portion 213 acts as a flow guiding region inhibiting a fluid from flowing into the first lumen 10a via the first distal end opening portion 211h while also inhibiting a fluid flowing out from the first lumen 10a from exiting the first distal end opening portion 211h, due to a perfusion of a fluid which is supplied to the first lumen 10a and flows to the second lumen 10b. The operation of the outflow/inflow inhibiting portion 213 will be described below in detail in the following description of a method of using the catheter device 1.

The length of the outflow/inflow inhibiting portion 213 in an axial direction which is set by the distance between the first distal end opening portion 211h and the second distal end opening portion 212h is not particularly limited. The longer the length in the axial direction, the higher the effect of inhibiting a fluid from flowing into the first lumen 10a or flowing out from the first lumen 10a via the first distal end opening portion 211h. On the other hand, if the length of the outflow/inflow inhibiting portion 213 in the axial direction is excessively long, an aspiration force for aspirating blood from a living body via the first distal end opening portion 211h becomes dissipated. From the viewpoint described above, it is preferable to select a suitable length for the length of the outflow/inflow inhibiting portion 213 in the axial direction that optimizes performance based on the fluid properties and desired flow volumes.

The hub 22 includes an outer tube hub 221 which is disposed in the proximal portion of the outer tube 211, and an inner tube hub 222 which is disposed in the proximal portion of the inner tube 212. The outer tube hub 221 and the inner tube hub 222 are integrally configured to be interlocked with each other by an interlock portion 22a (refer to FIG. 3).

With reference to FIG. 1 again, the catheter main body 30 includes a first tube section 31 which causes the blood collecting needle 20 and the supply section 41 to communicate with each other; a second tube section 32 which causes the blood collecting needle 20, the aspiration pump 42, and a switch valve 37 (which will be described below) to communicate with each other; a liquid discharging tube 33 arranged to selectably receive a flow from the second tube 32 via valve 37; an initial flowing blood tube 34 arranged to selectably receive a flow from the second tube 32 via valve 37; and a main blood collecting tube 35 arranged to selectably receive a flow from the second tube 32 via valve 37. The catheter main body 30 further includes a bifurcating connector 36 from which the first tube 31 and the second tube 32 are separately connected; the switch valve 37 which selectively switches a flow path from the second lumen 10b toward one of tubes 33, 34, or 35; and a connection section 38 which liquid-tightly connects the blood collecting needle 20, the first tube 31, and the second tube 32.

In a state where the connection section 38 of the catheter main body 30 is connected to the hub 22 of the blood collecting needle 20, the outer tube 211 and the first tube 31 form the flow path of the first lumen 10a, and the inner tube 212 and the second tube 32 form the flow path of the second lumen 10b.

The first tube 31 causes the connection section 38 to communicate with the supply section 41 via the bifurcating connector 36 to receive the flushing liquid. The first tube 31 includes a distal side first tube 31d which couples the connection section 38 to the bifurcating connector 36, and a proximal side first tube 31p which couples the bifurcating connector 36 to the supply of a flushing liquid holding unit 411 of the supply section 41 (which will be described below).

The second tube 32 causes the connection section 38 to communicate with an inlet of the switch valve 37 via the bifurcating connector 36. The second tube 32 includes a distal side second tube 32d which is disposed in a lumen of the first tube 31, and a proximal side second tube 32p which causes the bifurcating connector 36 to communicate with the inlet of the switch valve 37.

The distal side second tube 32d is disposed inside the distal side first tube 31d. Accordingly, the distal side second tube 32d and the distal side first tube 31d have a double tube structure. The first lumen 10a is formed in a part partitioned between the distal side second tube 32d and the distal side first tube 31d.

The liquid discharging tube 33 causes a respective outlet of the switch valve 37 and the waste liquid tank 60 to communicate with each other and guides a fluid, which has flowed in via the second tube 32, to the waste liquid tank 60.

The initial flowing blood tube 34 causes a respective outlet of the switch valve 37 and the initial flowing blood bag 51 to communicate with each other and guides initial flowing blood, which has flowed in via the second tube 32, to the initial flowing blood bag 51.

The main blood collecting tube 35 causes a respective outlet of the switch valve 37 and the main blood collecting bag 53 to communicate with each other and guides blood, which has flowed in via the second tube 32, to the main blood collecting bag 53.

For example, the first tube 31, the second tube 32, the liquid discharging tube 33, the initial flowing blood tube 34, and the main blood collecting tube 35 can be formed of a known resin such as urethane, polyurethane, silicon, and vinyl chloride.

For example, the bifurcating connector 36 may include a T-tube (refer to FIG. 1) or a Y-tube.

The switch valve 37 includes a known electromagnetic valve or the like. The switch valve 37 is connected to the second tube 32 and switches the flow path from the second lumen 10b over to the liquid discharging tube 33, the initial flowing blood tube 34, or the main blood collecting tube 35. Accordingly, the switch valve 37 selectively switches among the state of communication between the second lumen 10b and the waste liquid tank 60, the state of communication between the second lumen 10b and the initial flowing blood bag 51, and the state of communication with the main blood collecting bag 53.

The switch valve 37 is not limited to the above configuration as long as the flow path of a fluid flowing in each tube can be opened and closed. For example, the switch valve 37 may include a clamping member or the like which clamps each tube and blocks the flow path of a fluid.

The connection section 38 is configured to be fitted into the hub 22 of the blood collecting needle 20 and to be liquid-tightly connected thereto. The connection section 38 includes an outer tube connection section 381 which can be connected to the outer tube hub 221, and an inner tube connection section 382 which can be connected to the inner tube hub 222. The outer tube connection section 381 and the inner tube connection section 382 are integrally configured to be interlocked with each other by an interlock portion 38a (refer to FIG. 3).

The supply section 41 includes the flushing liquid holding unit 411 which holds a flushing liquid, and a supply pump 412 which supplies a flushing liquid from the flushing liquid holding unit 411 to the catheter main body 30.

The flushing liquid holding unit 411 is connected to the proximal end of the proximal side first tube 31p. The flushing liquid holding unit 411 is a medical bag which holds a medical liquid such as a flushing liquid. For example, a physiological salt solution can be used as a flushing liquid.

The supply pump 412 is disposed in the proximal side first tube 31p and guides a flushing liquid supplied from the flushing liquid holding unit 411 toward the distal side of the first tube 31.

The aspiration pump 42 is disposed in the proximal side second tube 32p and guides a fluid from the distal side of the second tube 32 toward the proximal side.

The initial flowing blood bag 51 stores initial flowing blood which has been guided via the initial flowing blood tube 34.

The sampling port 52 is connected to the initial flowing blood bag 51. The sampling port 52 is configured to be able to collect initial flowing blood for inspection when a blood transfer tube (not illustrated) is connected thereto.

The main blood collecting bag 53 stores blood which has been guided via the main blood collecting tube 35.

For example, the initial flowing blood bag 51 and the main blood collecting bag 53 are formed to have a bag shape by causing flexible sheet members made of a soft resin such as polyvinyl chloride to overlap each other, and welding or bonding their circumferential edges through heat welding, high-frequency welding, or the like.

The control unit 70 is a control circuit comprising a microprocessor for executing various kinds of control of each of the parts described above and computation processing in accordance with a program. Each function of the catheter device 1 is performed when the control unit 70 executes a program corresponding thereto. Specifically, the control unit 70 controls the flow of a fluid inside the catheter 10 by controlling operations of the supply pump 412, the aspiration pump 42, and the switch valve 37.

Figure 4:
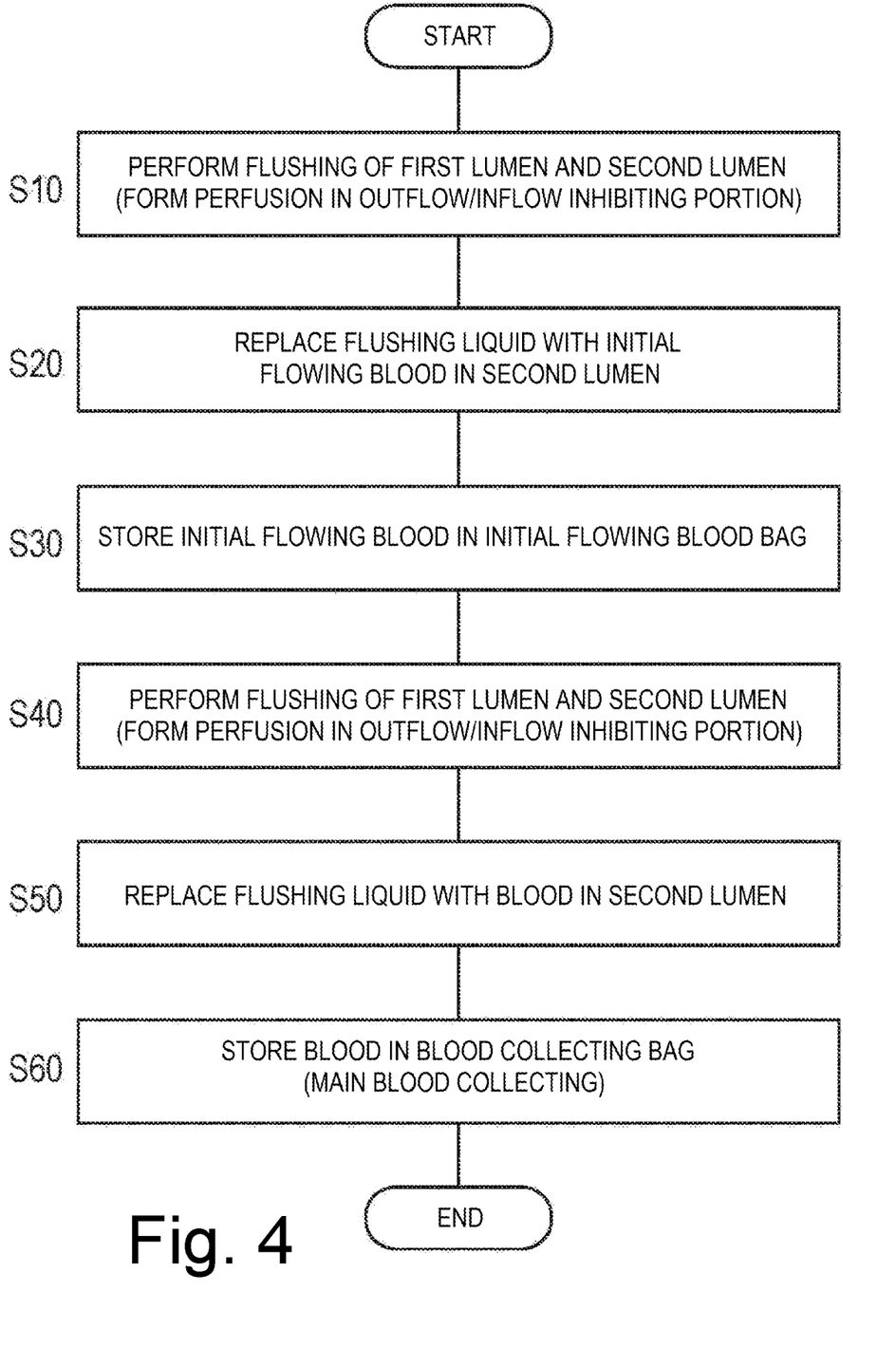
FIG. 4 is a flowchart for describing a method of using a catheter device according to the first embodiment.
Figure 5A:
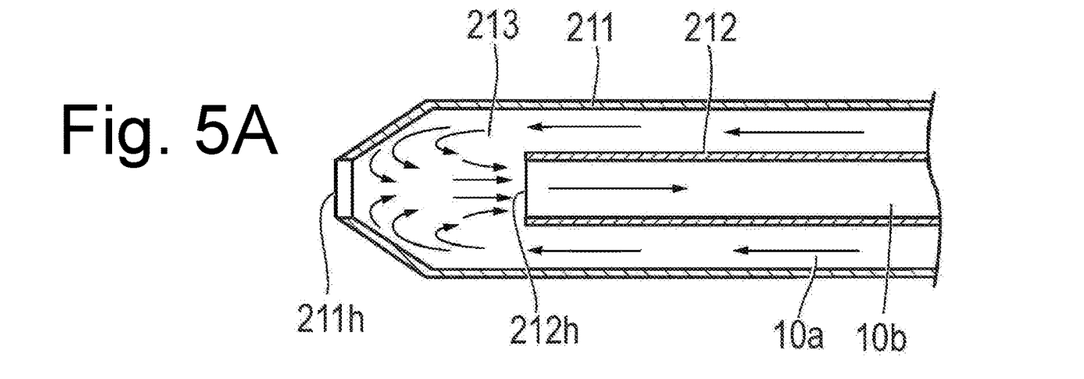
FIGS. 5A, 5B, and 5C are sectional views for describing an operation of the catheter according to the first embodiment.
Figure 5B:
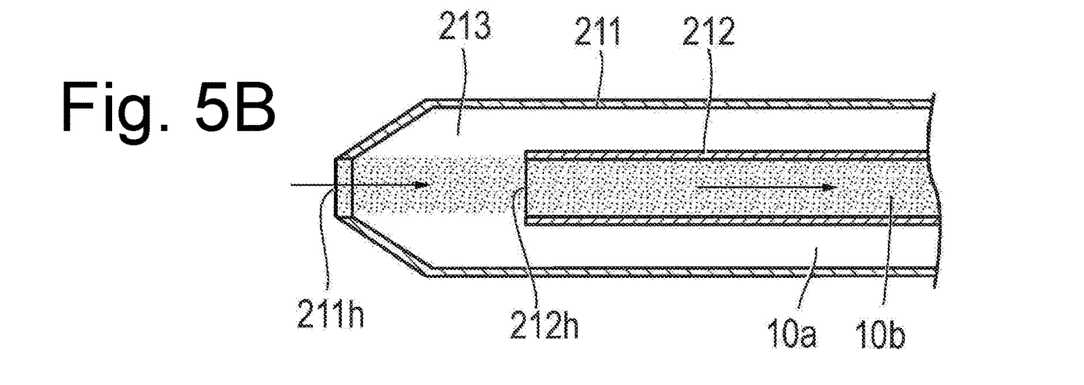
Figure 5C:
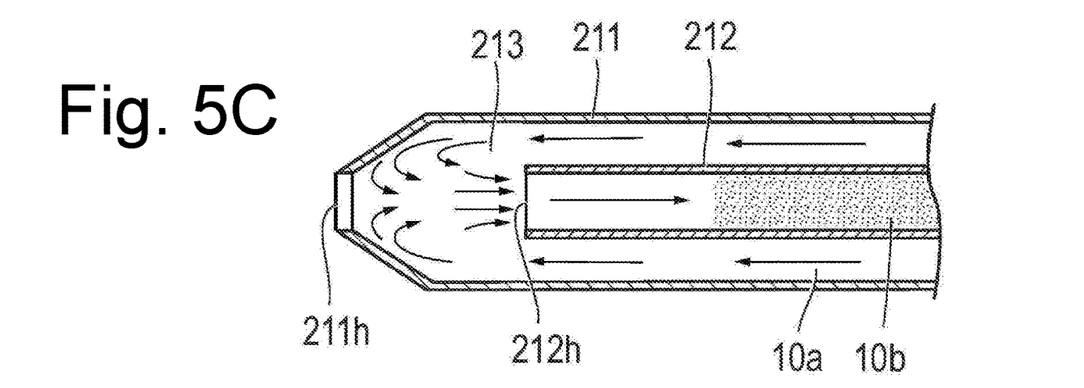

Hereinafter, the method of using the catheter device 1 according to the first embodiment will be described with reference to FIGS. 4 and 5. FIG. 4 is a flow chart for describing the method of using the catheter device 1 according to the present embodiment, and FIG. 5 is a view describing an operation of the catheter device 1.

First, a blood vessel is punctured by the distal portion of the outer tube 211 of the blood collecting needle 20. Accordingly, the distal portion including the first distal end opening portion 211h of the outer tube 211 is disposed inside the blood vessel.

Next, the hub 22 of the blood collecting needle 20 and the connection section 38 of the catheter main body 30 are connected to each other. A practitioner can respectively interlock the outer tube 211 and the inner tube 212 with the first tube 31 and the second tube 32 in a comparatively simple manner by connecting the hub 22 and the connection section 38 to each other. The outer tube 211 and the first tube 31 connected to each other form the first lumen 10a in their lumens, and the inner tube 212 and the second tube 32 connected to each other form the second lumen 10b in their lumens.

Next, flushing is performed by supplying a flushing liquid to the first lumen 10a and the second lumen 10b (Step S10). Specifically, first, the supply pump 412 and the aspiration pump 42 are operated to cause the second tube 32 and the liquid discharging tube 33 to communicate with each other by the switch valve 37.

A flushing liquid supplied by the supply pump 412 is guided to the distal side of the first lumen 10a. The second lumen 10b aspirated by the aspiration pump 42 is under a negative pressure. A flushing liquid guided to the outflow/inflow inhibiting portion 213 of the blood collecting needle 20 via first lumen 10a is drawn into the second lumen 10b via the second distal end opening portion 212h by utilizing this negative pressure. Accordingly, as illustrated in FIG. 5A, in the outflow/inflow inhibiting portion 213, a convective flow is generated due to a perfusion of a fluid, that is, a flushing liquid which is supplied to the first lumen 10a and reverses direction within inhibiting portion 213 to flow into the second lumen 10b.

Due to the flow of a flushing liquid caused by the convective flow, a fluid other than a flushing liquid is restrained from flowing in from the outflow/inflow inhibiting portion 213. Accordingly, the flow path of the first distal end opening portion 211h that would otherwise cause the inside of a blood vessel and the first lumen 10a to communicate with each other is inhibited/blocked.

In Step S10, it is preferable that the control unit 70 controls operations of the supply pump 412 and the aspiration pump 42 such that the supplying amount of a flushing liquid supplied to the first lumen 10a becomes larger than the aspirating amount of a fluid aspirated from the second lumen 10b. Accordingly, an accumulated state of a flushing liquid can be formed in the outflow/inflow inhibiting portion 213. Therefore, it is possible to more reliably block the flow path of the first distal end opening portion 211h causing the inside of a blood vessel and the first lumen 10a to communicate with each other.

As described above, the outflow/inflow inhibiting portion 213 inhibits blood from flowing into the first lumen 10a via the first distal end opening portion 211h and inhibits a flushing liquid, air, or a residue of blood or the like from flowing out from the first lumen 10a via the first distal end opening portion 211h, due to a perfusion of a fluid which is supplied to the first lumen 10a and is redirected by aspiration to flow to the second lumen 10b.

A flushing liquid which has flowed in via the second lumen 10b is guided by the aspiration pump 42 and is discharged to the waste liquid tank 60 via the second tube 32 and the liquid discharging tube 33, together with air or a residue of blood or the like. Accordingly, air or a residue is discharged from the first lumen 10a and the second lumen 10b, and the first lumen 10a and the second lumen 10b are filled with a flushing liquid.

Next, in the second lumen 10b, catheter device 1 is reconfigured so that the flushing liquid is replaced with initial flowing blood (Step S20). Specifically, first, while maintaining a state where the aspiration pump 42 is operated and a state where the second tube 32 and the liquid discharging tube 33 communicate with each other, the supply pump 412 is stopped. Accordingly, a flushing liquid is no longer supplied to the outflow/inflow inhibiting portion 213. Therefore, a perfusion of a fluid flowing from the first lumen 10a to the second lumen 10b is not generated, so that the flow path between the inside of a blood vessel and the first lumen 10a is opened in the first distal end opening portion 211h, and the outflow/inflow inhibiting portion 213 allows initial flowing blood to flow in from the inside of a blood vessel.

The aspiration pump 42 aspirates initial flowing blood from the first distal end opening portion 211h of the outer tube 211 which indwells in a living body and guides the initial flowing blood to the second lumen 10b as illustrated in FIG. 5B. Blood guided to the second lumen 10b pushes out the flushing liquid present in the second lumen 10b to the proximal side. The pushed-out flushing liquid is discharged to the waste liquid tank 60 via the liquid discharging tube 33. Accordingly, in the second lumen 10b, the flushing liquid is replaced with initial flowing blood.

Next, while maintaining a state where the supply pump 412 is stopped and a state where the aspiration pump 42 is operated, the second tube 32 and the initial flowing blood tube 34 are caused to communicate with each other by the switch valve 37. Accordingly, the initial flowing blood is guided to the initial flowing blood bag 51 via the second tube 32 and the initial flowing blood tube 34 and is stored therein (Step S30). When necessary, the initial flowing blood is collected to a blood transfer tube (not illustrated) through the sampling port 52 and is used in various blood inspections.

Next, an operation similar to that of Step S10 is performed, such that the first lumen 10a and the second lumen 10b are flushed in Step S40. Specifically, first, the supply pump 412 and the aspiration pump 42 are operated to cause the second tube 32 and the liquid discharging tube 33 to communicate with each other by the switch valve 37. Accordingly, similar to Step S10, air or a residue of blood or the like inside the outer tube 211, the inner tube 212, the first tube 31, and the second tube 32 is discharged, and they are filled with a flushing liquid. In addition, during flushing, as illustrated in FIG. 5C, in the outflow/inflow inhibiting portion 213, a convective flow is generated due to a perfusion of a fluid, that is, a flushing liquid which is supplied to the first lumen 10a and flows to the second lumen 10b. Therefore, the flow path of the first distal end opening portion 211h causing the inside of a blood vessel and the first lumen 10a to communicate with each other is blocked. Accordingly, the outflow/inflow inhibiting portion 213 can inhibit a flushing liquid, air, or a residue of blood or the like from flowing out into a blood vessel via the first distal end opening portion 211h and can inhibit blood from flowing into the first lumen 10a via the first distal end opening portion 211h.

In Step S40, after initial flowing blood is collected, the initial flowing blood or air is eliminated by flushing the first lumen 10a and the second lumen 10b, so that only fresh blood can be collected through main blood collecting in the next step.

Next, an operation similar to that of Step S20 is performed, such that the flushing liquid is replaced with blood in the second lumen 10b (Step S50).

In Step S50, while maintaining a state where the supply pump 412 is stopped and a state where the aspiration pump 42 is operated, the second tube 32 and the main blood collecting tube 35 are caused to communicate with each other by the switch valve 37. Accordingly, blood is guided to the main blood collecting bag 53 via the second tube 32 and the main blood collecting tube 35 and is stored therein (Step S60).

As described above, the blood collecting needle 20 of the catheter 10 according to the present embodiment includes the outer tube 211 which includes the first distal end opening portion 211h to be introduced into a living body and in which the first lumen 10a capable of circulating a fluid is formed; the inner tube 212 which is disposed in the first lumen 10a, which includes the second distal end opening portion 212h positioned closer to the proximal side than the first distal end opening portion 211h, and in which the second lumen 10b capable of circulating a fluid is formed; and the outflow/inflow inhibiting portion 213 which is partitioned in the first lumen 10a between the first distal end opening portion 211h and the second distal end opening portion 212h and inhibits a fluid from flowing out from the first lumen 10a or a fluid from flowing into the first lumen 10a via the first distal end opening portion 211h, due to a perfusion of a fluid which is supplied to the first lumen 10a and flows to the second lumen 10b.

According to the catheter 10 having such a configuration, blood can be collected from a living body via the first distal end opening portion 211h of the outer tube 211. In addition, when the catheter 10 is flushed, a convective flow can be formed in the outflow/inflow inhibiting portion 213 due to a perfusion of a flushing liquid which is supplied to the first lumen 10a and flows to the second lumen 10b. Due to the convective flow, in the outflow/inflow inhibiting portion 213, the flow path of the first distal end opening portion 211h causing the inside of a blood vessel and the first lumen 10a to communicate with each other is blocked. Accordingly, when flushing is performed, a flushing liquid, air, or a residue of blood or the like can be inhibited from flowing out into a blood vessel via the first distal end opening portion 211h, and blood can be inhibited from flowing into the first lumen 10a via the first distal end opening portion 211h. Therefore, blood collecting and flushing can be performed in a noninvasive manner.

In addition, since the central axis of the outer tube 211 is configured to overlap the central axis of the inner tube 212, the first lumen 10a formed in the gap between the outer tube 211 and the inner tube 212 has a uniform size in the circumferential direction. Therefore, in the first lumen 10a, a uniform flow having no turbulence can be formed. Accordingly, a uniform perfusion having no bias can be formed in the first lumen 10a and the second lumen 10b. Therefore, a convective flow can be more stably formed. Therefore, the outflow/inflow inhibiting portion 213 can more reliably block the flow path of the first distal end opening portion 211h causing the inside of a blood vessel and the first lumen 10a to communicate with each other.

The catheter device 1 according to the present embodiment further includes the supply section 41 which supplies a flushing liquid to the first lumen 10a, an aspiration unit 42 which aspirates blood from a living body via the second lumen 10b, and the control unit 70 which controls operations of the supply section 41 and the aspiration unit 42. The control unit 70 controls operations of the supply section 41 and the aspiration unit 42 to form a perfusion of a flushing liquid, which is supplied to the first lumen 10a and is aspirated into the second lumen 10b, in the outflow/inflow inhibiting portion 213 and inhibits a fluid from flowing out from the first lumen 10a or a fluid from flowing into the first lumen 10a via the first distal end opening portion 211h, due to the perfusion.

According to the catheter device 1 having such a configuration, the supplying amount of a flushing liquid and the aspirating amount of a fluid can be precisely controlled by the supply pump 412 and the aspiration unit 42. Accordingly, even if flushing is continuously performed for a long time, a volume of flushing liquid that is supplied is no more than necessary. In addition, when flushing is performed, in the outflow/inflow inhibiting portion 213, the flow path of the first distal end opening portion 211h causing the inside of a blood vessel and the first lumen 10a to communicate with each other can be blocked. Accordingly, when the catheter 10 is flushed, a flushing liquid, air, or a residue of blood or the like can be inhibited from flowing out from catheter 10 into a blood vessel via the first distal end opening portion 211h, and blood can be inhibited from flowing into the first lumen 10a via the first distal end opening portion 211h. Accordingly, blood collecting and flushing can be performed in a low invasive manner.

In addition, the catheter device 1 further includes the initial flowing blood bag 51 which stores initial flowing blood; the blood collecting bag 53 which stores collected blood; the waste liquid tank 60 which stores a fluid to be discarded; and the switch valve 37 which is capable of selectively switching among a communication state between the second lumen 10b and the initial flowing blood bag 51, a communication state between the second lumen 10b and the blood collecting bag 53, and a communication state between the second lumen 10b and the waste liquid tank 60. Accordingly, initial flowing blood for inspection and blood for blood collecting can be separately collected. In addition, after initial flowing blood is collected, the initial flowing blood or air is eliminated by flushing the first lumen 10a and the second lumen 10b, so that fresh blood can be collected through main blood collecting in the next step.

Second Embodiment

Figure 6:
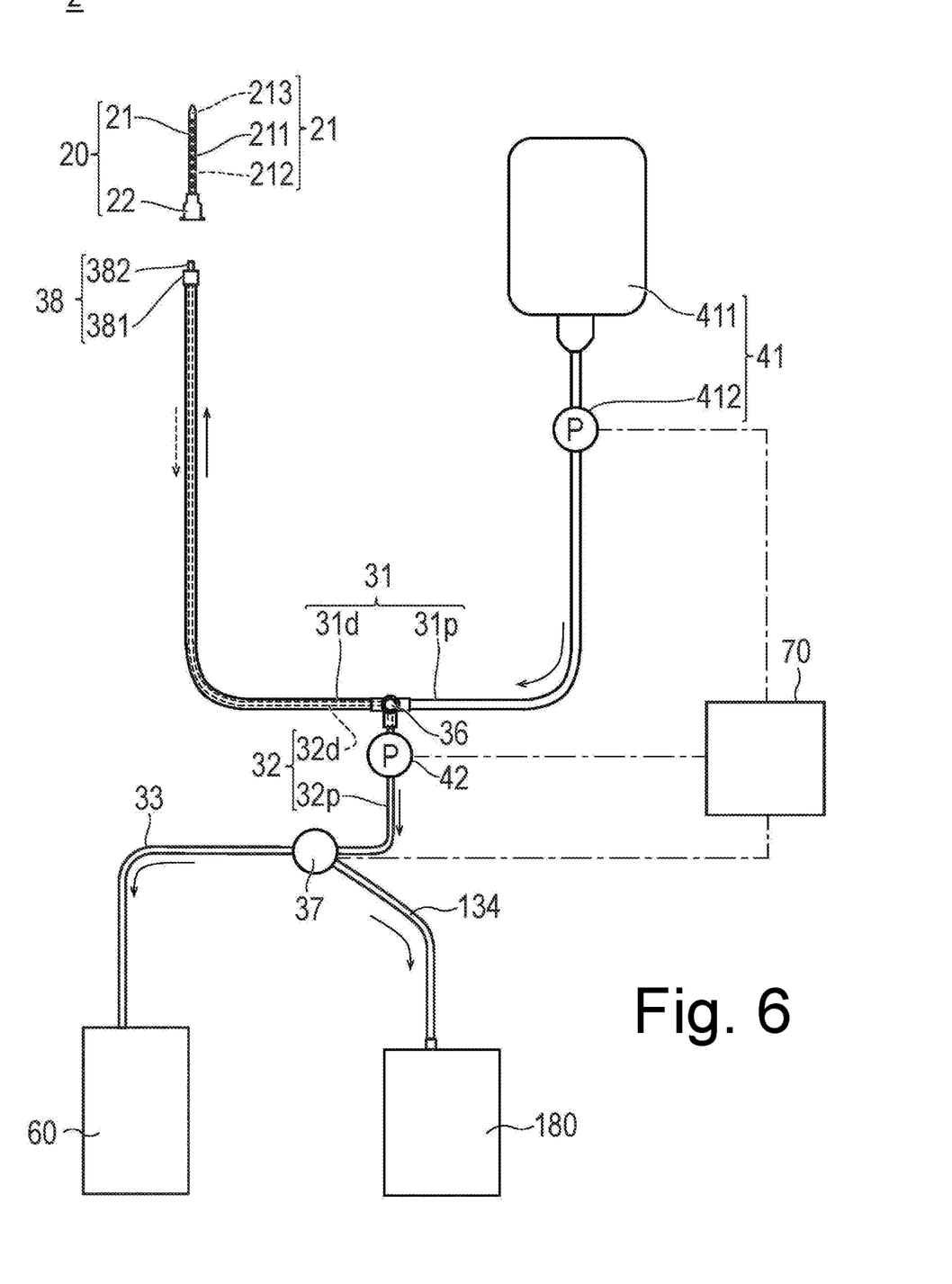
FIG. 6 is a view schematically illustrating the entirety of a catheter device according to a second embodiment.
Figure 7:
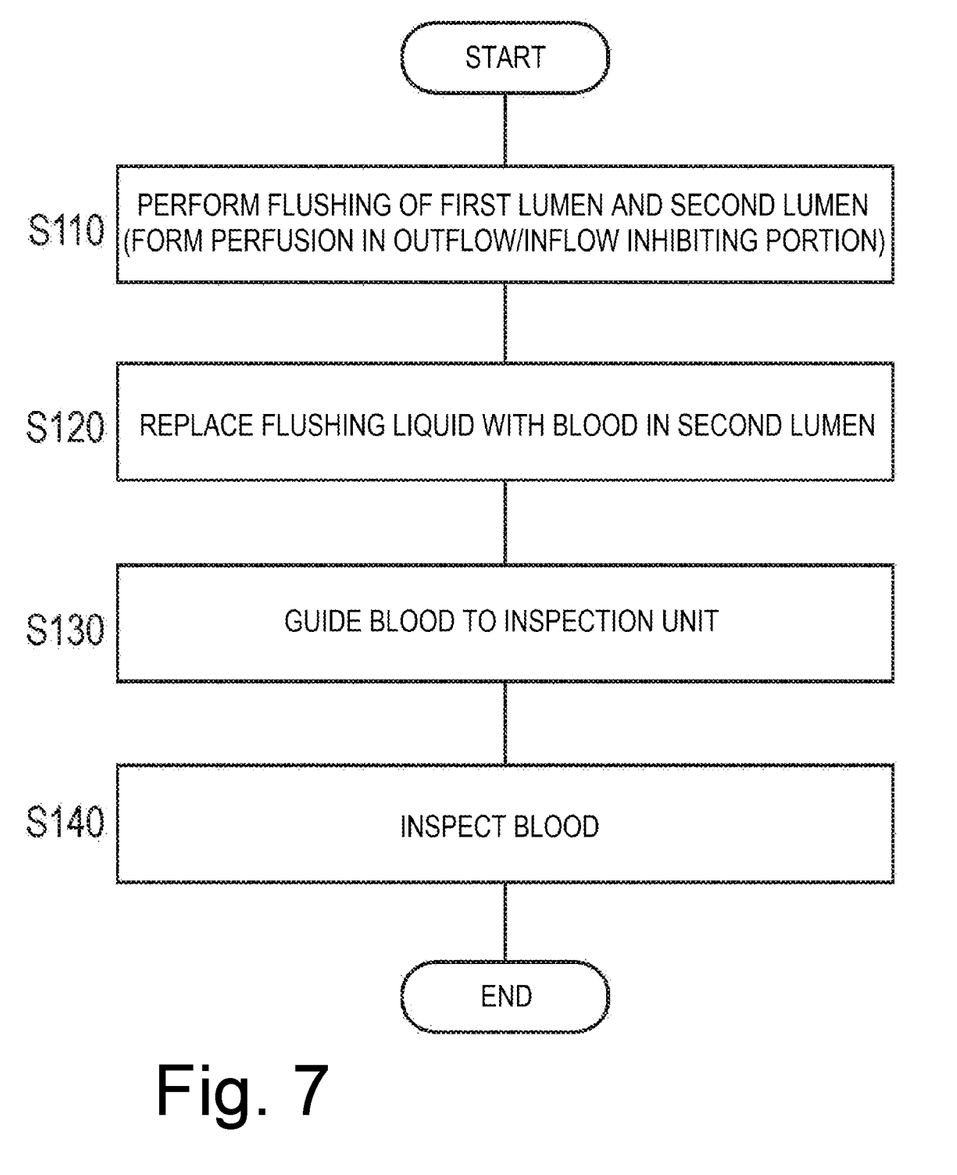
FIG. 7 is a flowchart for describing a method of using a catheter device according to the second embodiment.

With reference to FIGS. 6 and 7, a catheter device 2 according to a second embodiment will be described. FIG. 6 is a view schematically illustrating the entirety of the catheter device 2 according to the second embodiment, and FIG. 7 is a flow chart for describing a method of using the catheter device 2.

The catheter device 2 according to the second embodiment is employed to perform a predetermined blood inspection/analysis using collected blood. The catheter device 2 differs from that in the first embodiment described above in including an inspection tube 134 and an inspection unit 180 which performs a blood inspection, in place of the initial flowing blood tube 34, the main blood collecting tube 35, the initial flowing blood bag 51, and the main blood collecting bag 53. The same reference signs are applied to parts having the same function as those in the first embodiment described above, and description thereof will be omitted.

As illustrated in FIG. 6, the switch valve 37 is connected to the second tube 32 and switches a flow path from the second tube 32 over to the liquid discharging tube 33 or the inspection tube 134. Accordingly, the switch valve 37 selectively switches between a communication state between the second lumen 10b and the inspection unit 180, and a communication state between the second lumen 10b and the waste liquid tank 60.

The inspection tube 134 causes the switch valve 37 and the inspection unit 180 to communicate with each other.

The inspection unit 180 performs an inspection of blood guided from the inspection tube 134. A blood inspection widely includes clinical inspections, such as a biochemical inspection, in which the state of a disease or the like is examined by utilizing blood. Examples thereof include a component inspection of measuring a blood glucose level, pH, O$_2$, K$^+$, and the like, a clotting inspection inspecting a clotting rate of blood, and a blood pressure inspection measuring a blood pressure.

Hereinafter, the method of using the catheter device 2 according to the second embodiment will be described with reference to FIG. 7. FIG. 7 is a flow chart for describing the method of using the catheter device 2 according to the present embodiment.

Since the procedures of flushing the first lumen 10a and the second lumen 10b (Step S110) and replacing a flushing liquid with blood in the second lumen 10b (Step S120) are similar to those of Steps S10 and S20 (refer to FIG. 4) in the first embodiment described above, description thereof will be omitted.

In Step S130, while maintaining a state where the supply pump 412 is stopped and a state where the aspiration pump 42 is operated, the second tube 32 and the inspection tube 134 are caused to communicate with each other by the switch valve 37. Accordingly, blood is guided to the inspection unit 180.

Next, in Step S140, an inspection of blood guided by the inspection unit 180 is performed. A monitor or the like may display obtained inspection results such that the results can be visually recognized.

As described above, the catheter device 2 according to the second embodiment has a similar operational effect due to a configuration similar to that of the first embodiment described above.

In addition, the catheter device 2 has the inspection unit 180 which performs an inspection of blood guided by the aspiration pump 42, the waste liquid tank 60 which stores a fluid to be discarded, and the switch valve 37 which is capable of selectively switching between a communication state between the second lumen 10b and the inspection unit 180, and a communication state between the second lumen 10b and the waste liquid tank 60. Accordingly, an inspection of collected blood and flushing can be efficiently performed.

Third Embodiment

Figure 8:
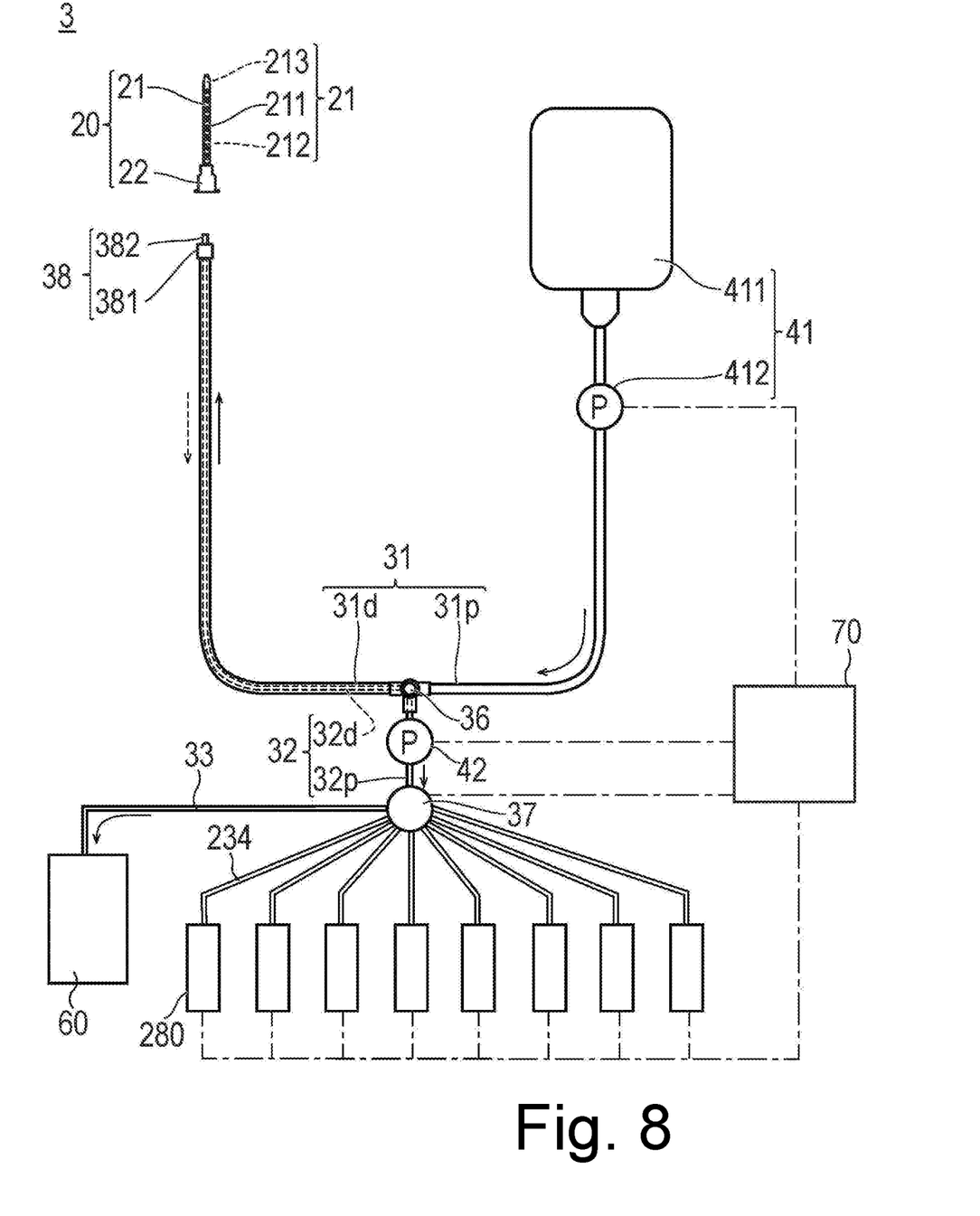
FIG. 8 is a view schematically illustrating the entirety of a catheter device according to a third embodiment.
Figure 9:
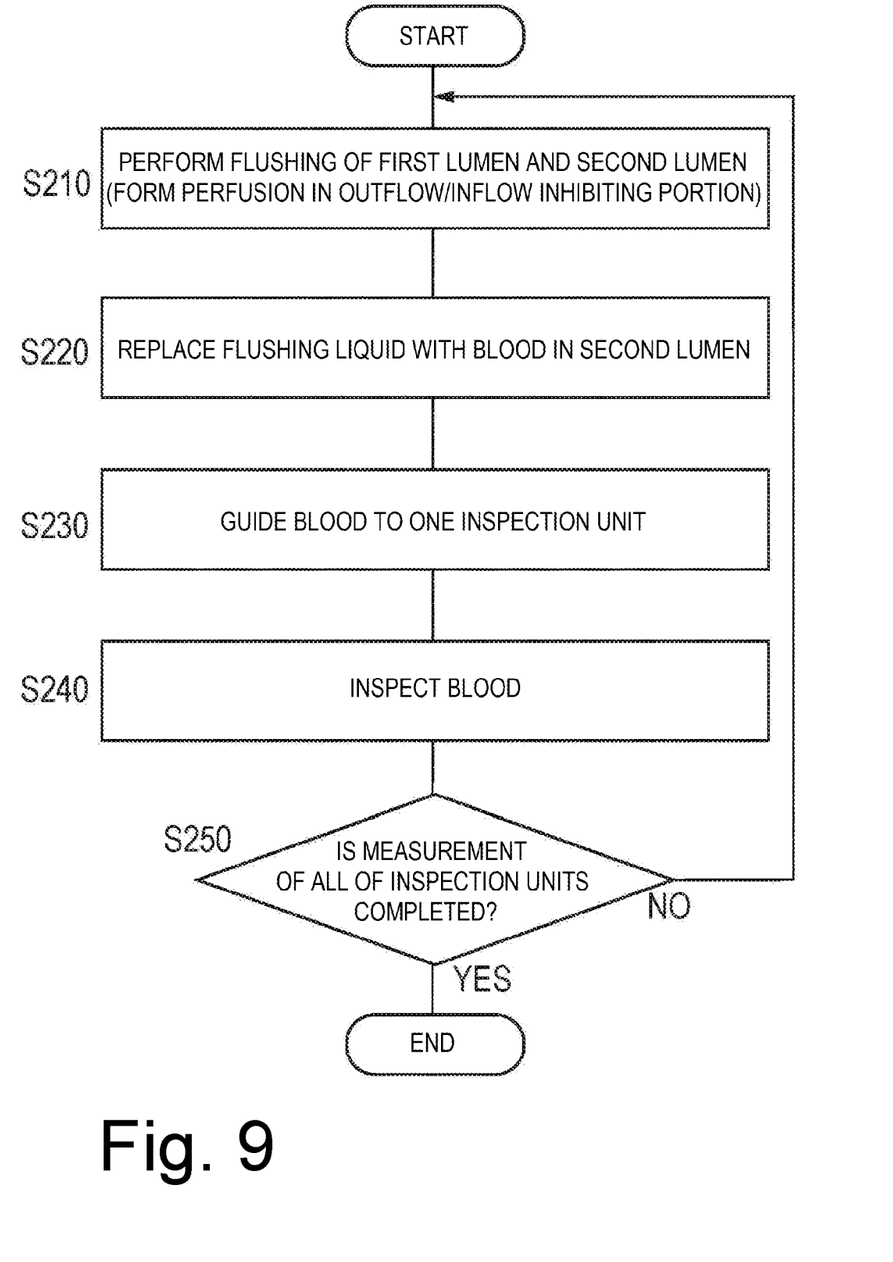
FIG. 9 is a flowchart for describing a method of using a catheter device according to the third embodiment.

With reference to FIGS. 8 and 9, a catheter device 3 according to a third embodiment will be described. FIG. 8 is a view schematically illustrating the entirety of the catheter device 3 according to the third embodiment, and FIG. 9 is a flow chart for describing a method of using the catheter device 3.

The catheter device 3 according to the third embodiment is employed to repetitively perform a predetermined blood inspection a plurality of times using collected blood. The catheter device 3 according to the third embodiment differs from that in the second embodiment described above in including a plurality of inspection tubes 234 and a plurality of inspection units 280. The same reference signs are applied to parts having the same function as those in the second embodiment described above, and description thereof will be omitted.

As illustrated in FIG. 8, the switch valve 37 is connected to the second tube 32 and switches a flow path from the second tube 32 over to the liquid discharging tube 33 or one inspection tube 234 of the plurality of inspection tubes 234. Accordingly, the switch valve 37 selectively switches between a communication state between the second lumen 10b and one inspection unit 280 of the plurality of inspection units 280, and a communication state between the second lumen 10b and the waste liquid tank 60.

The inspection tubes 234 causes the switch valve 37 and the inspection units 280 to communicate with each other.

There are provided a plurality of inspection tubes 234 as many as the inspection units 280. One inspection tube 234 communicates with one inspection unit 280. The numbers of the inspection tubes 234 and the inspection units 280 are not particularly limited and can suitably vary in accordance with the desired number of times of inspections or the like.

The inspection units 280 performs an inspection of blood guided from the inspection tubes 234.

Hereinafter, the method of using the catheter device 3 according to the third embodiment will be described with reference to FIG. 9. FIG. 9 is a flow chart for describing the method of using the catheter device 3 according to the present embodiment.

Since the procedures of cleaning the first lumen 10a and the second lumen 10b (Step S210) and replacing a flushing liquid with blood in the second lumen 10b (Step S220) are similar to those of Steps S10 and S20 (refer to FIG. 4) in the first embodiment described above, description thereof will be omitted.

In Step S230, while maintaining a state where the supply pump 412 is stopped and a state where the aspiration pump 42 is operated, the second tube 32 and one inspection tube 234 are caused to communicate with each other by the switch valve 37. Accordingly, blood is guided to one inspection unit 280 via one inspection tube 234.

Next, in Step S240, a blood inspection is performed by using one inspection unit 280.

Next, in Step S250, Steps S210 to S240 are performed for each of the remaining unused inspection units 280 (Step S250: NO), and when measurement of all of the inspection units 280 is completed, a plurality of inspection results are obtained (Step S250: YES).

As described above, the catheter device 3 according to the third embodiment has a similar operational effect due to a configuration similar to that of the first embodiment described above.

In addition, the catheter device 3 has the plurality of inspection units 280, and the switch valve 37 selectively switches a communication state between the second lumen 10b, and the plurality of inspection units 280 and the waste liquid tank 60. Accordingly, an inspection of blood can be repetitively performed a plurality of times by using the plurality of inspection units 280. Therefore, for example, even in a case where an inspection unit 280 for single use is used, a chronological change in a blood condition can be measured.

Hereinabove, the catheter and the catheter device according to the present invention have been described through the embodiments and a modification example. However, the present invention is not limited to only the configurations described in the embodiments and the modification example and can be suitably changed based on the disclosure of the patent.

For example, the catheter includes the blood collecting needle having the outflow/inflow inhibiting portion. However, as long as a fluid can be inhibited from flowing out and flowing in due to a perfusion of a fluid which is supplied to the first lumen and flows to the second lumen, the configuration is not limited to that including the blood collecting needle. For example, the outflow/inflow inhibiting portion may include a tube having a double tube structure.

In addition, the configuration of respectively interlocking the outer tube and the inner tube of the blood collecting needle with the first tube and the second tube is not limited to a configuration provided with the hub of the blood collecting needle and the connection section which can be fitted and connected to each other. For example, the first tube and the second tube may be respectively interlocked with the outer tube and the inner tube by being individually screwed therein in a linear manner.

In addition, the disposing locations and the numbers of the supply pump, the aspiration pump, and the switch valve included in the catheter device are not particularly limited and can be suitably changed.

What is claimed is:

1. A catheter device comprising:
   an outer tube having a first distal end opening adapted to be introduced into a living body, the outer tube defining a first lumen capable of circulating a flushing liquid toward the first distal end opening;
   an inner tube disposed in the first lumen and having a second distal end opening proximally spaced from the first distal end opening, the inner tube defining a second lumen capable of circulating the flushing liquid away from the second distal end, wherein a space axially disposed between the first distal end opening and the second distal end opening defines an outflow/inflow inhibiting portion which inhibits a flow of the flushing liquid out from the first lumen into the living body via the first distal end opening as a result of a perfusion of the flushing fluid being supplied through the first lumen and into the second lumen via the outflow/inflow inhibiting portion;
   a supply section which supplies the flushing liquid to the first lumen;
   an aspiration unit which aspirates the flushing liquid via the second lumen; and
   a control unit which controls operations of the supply section and the aspiration unit,
   wherein the control unit controls operations of the supply section and the aspiration unit to form the perfusion of the flushing liquid, which is supplied to the first lumen and is aspirated into the second lumen, in the outflow/inflow inhibiting portion and inhibits the flushing liquid from flowing out from the first lumen or a fluid from flowing into the first lumen via the first distal end opening, due to the perfusion.

2. The catheter device according to claim 1, further comprising:
   an initial flowing blood bag which stores initial flowing blood;
   a blood collecting bag which stores subsequently collected blood;
   a waste liquid tank which stores a waste fluid to be discarded; and
   a switch valve adapted to selectively switch among a communication state between the second lumen and the initial flowing blood bag, a communication state between the second lumen and the blood collecting bag, and a communication state between the second lumen and the waste liquid tank.

3. The catheter device according to claim 1, further comprising:
   an inspection tube configured to guide blood from the aspiration unit for measurement of a blood condition;
   a waste liquid tank which stores a waste fluid to be discarded; and
   a switch valve adapted to selectively switch between a communication state between the second lumen and the inspection tube, and a communication state between the second lumen and the waste liquid tank.

4. The catheter device according to claim 3, further comprising:
   a plurality of inspection tubes,
   wherein the switch valve selectively switches between a communication state between the second lumen and one inspection tube of the plurality of inspection tubes, and a communication state between the second lumen and the waste liquid tank.

5. A method of collecting blood, comprising the steps of:
   inserting a distal end of a catheter into a blood vessel, wherein the catheter has an outer tube with a first distal end opening and defining a first lumen capable of circulating a fluid toward the first distal end opening, wherein the catheter has an inner tube disposed in the first lumen defining a second lumen with a second distal end opening proximally spaced from the first distal end opening, and wherein a space axially disposed between the first distal end and the second distal end defines an outflow/inflow inhibiting portion;
   supplying a flushing liquid to the first lumen via a supply pump;
   aspirating a proximal end of the second lumen to a waste tank via an aspirating pump and a switching valve to flush the catheter, whereby perfusion of the flushing liquid through the first lumen and into the second lumen via the outflow/inflow inhibiting portion inhibits any flow directed out from the first lumen into the blood vessel;
   deactivating the supply pump and aspirating the proximal end of the second lumen into an initial blood bag via the aspirating pump and the switching valve, whereby blood is collected through the distal end of the catheter;
   supplying the flushing liquid to the first lumen via the supply pump;
   aspirating the proximal end of the second lumen to the waste tank via the aspirating pump and the switching valve to flush the catheter, whereby perfusion of the flushing liquid through the first lumen and into the second lumen via the outflow/inflow inhibiting portion inhibits any flow directed out from the first lumen into the blood vessel; and
   deactivating the supply pump and aspirating the proximal end of the second lumen into a main blood collector via the aspirating pump and the switching valve, whereby blood is collected through the distal end of the catheter.

6. The method of claim 5 wherein the main blood collector is comprised of a main blood bag.

7. The method of claim 5 wherein the main blood collector is comprised of an inspection tube configured to guide blood for measurement of a blood condition, the method further comprising the step of:
   measuring a property of the blood guided by the inspection tube.

* * * * *